(12) United States Patent
Zuo et al.

(10) Patent No.: US 11,622,875 B2
(45) Date of Patent: *Apr. 11, 2023

(54) INTESTINAL BARRIER SLEEVE RELEASE SYSTEM

(71) Applicant: HANGZHOU TANGJI MEDICAL TECHNOLOGY CO., LTD., Hangzhou (CN)

(72) Inventors: Yuxing Zuo, Hangzhou (CN); Yan Lu, Hangzhou (CN)

(73) Assignee: HANGZHOU TANGJI MEDICAL TECHNOLOGY CO., LTD., Hangzhou (CN)

( * ) Notice: Subject to any disclaimer, the term of this patent is extended or adjusted under 35 U.S.C. 154(b) by 488 days.

This patent is subject to a terminal disclaimer.

(21) Appl. No.: 16/482,034

(22) PCT Filed: Jun. 28, 2017

(86) PCT No.: PCT/CN2017/090466
§ 371 (c)(1),
(2) Date: Jul. 30, 2019

(87) PCT Pub. No.: WO2018/196157
PCT Pub. Date: Nov. 1, 2018

(65) Prior Publication Data
US 2020/0000617 A1 Jan. 2, 2020

(30) Foreign Application Priority Data

Apr. 28, 2017 (CN) .......................... 201710293809.1

(51) Int. Cl.
A61F 5/00 (2006.01)
A61F 2/966 (2013.01)
A61F 2/04 (2013.01)

(52) U.S. Cl.
CPC ............ A61F 5/0076 (2013.01); A61F 2/966 (2013.01); A61F 5/0013 (2013.01);
(Continued)

(58) Field of Classification Search
CPC ...... A61F 5/0076; A61F 2/966; A61F 5/0013; A61F 5/0089; A61F 2002/045;
(Continued)

(56) References Cited

U.S. PATENT DOCUMENTS

2002/0099435 A1* 7/2002 Stinson ................... A61F 2/966
623/1.12
2004/0201216 A1* 10/2004 Segal .................... A61M 39/10
285/401

(Continued)

*Primary Examiner* — Susan S Su
*Assistant Examiner* — Ted Yang
(74) *Attorney, Agent, or Firm* — Li & Cai Intellectual Property (USA) Office

(57) ABSTRACT

An intestinal barrier sleeve release system includes a tubular housing having a first opening at one end and a second opening at the other end. A tubular sleeve to be released is disposed in the housing. A release body connected to the one end of the tubular sleeve is disposed at the first opening of the housing and is made of a material that can be dissolved and absorbed in human intestines. An inner sheath, a middle sheath and an outer sheath are sequentially set and move relative to each other. The inner sheath and the middle sheath are operated to move axially, the release body is disengaged from the housing, and the tubular sleeve moves out of the housing and is released at a specified position of the human intestines.

12 Claims, 3 Drawing Sheets

(52) U.S. Cl.
CPC ...... *A61F 5/0089* (2013.01); *A61F 2002/045* (2013.01); *A61F 2210/0004* (2013.01); *A61F 2210/0014* (2013.01); *A61F 2230/0071* (2013.01)

(58) Field of Classification Search
CPC ...... A61F 2210/0004; A61F 2210/0014; A61F 2230/0071
See application file for complete search history.

(56) References Cited

U.S. PATENT DOCUMENTS

| | | | |
|---|---|---|---|
| 2006/0009858 A1* | 1/2006 | Levine | A61F 5/0076 623/23.65 |
| 2006/0155312 A1* | 7/2006 | Levine | A61B 17/0482 606/153 |
| 2008/0195226 A1* | 8/2008 | Williams | A61F 2/04 623/23.67 |
| 2011/0004320 A1* | 1/2011 | Priplata | A61F 5/0076 623/23.65 |

* cited by examiner

INTESTINAL BARRIER SLEEVE RELEASE SYSTEM

CROSS-REFERENCE TO RELATED PATENT APPLICATION

This application claims the benefit of priority to China Patent Application No. 201710293809.1, filed on Apr. 28, 2017 in People's Republic of China. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a technical field of medical equipment, and more particularly to an intestinal barrier sleeve release system.

BACKGROUND OF THE DISCLOSURE

In recent years, people have paid more attention to diabetes. Diabetes is a common endocrine disease caused by fine dining and ingestion of more food, excessive nutrition intake and less exercising. Specifically, diabetes is a group of metabolic disorders characterized by high blood sugar, due to failure to produce enough insulin or respond to insulin properly or both. Serious long-term complications of diabetes include cardiovascular disease, chronic kidney disease, and damage to the eyes and nerves. Other complications of diabetes such as obesity also pose a great threat to people's health. Among adults over 20 years old in China, the prevalence of diabetes is 9.7%; that is, in China 150 million people have diabetes. Treatment of diabetes involves maintaining a healthy diet, regular physical exercise, and medication treatment, which requires persistence. If patients stop their diet, they will likely regain the weight or have rebound weight gain. Furthermore, constant medication treatment or insulin injection remain a financial burden and inconvenience in daily life.

Gastric bypass surgery also has tremendous effects in improving the symptoms of type 2 diabetes and obesity. In 2011, the International Diabetes Federation suggests that bariatric surgery (including gastric bypass) should be considered an appropriate treatment for severely obese patients with type 2 diabetes. However, as a surgical procedure, gastric bypass may leave surgical wound in human bodies, and involve the potential for complications which increase risk and mortality, such as bowel obstruction, anastomotic leakage, pulmonary embolism, deep vein thrombosis, portal vein thrombosis, and respiratory failure.

Some patients treat diabetes by inserting a kind of intestinal bypass liner. The intestinal bypass liner is complicated in structure and operation by having multiple lines to be pulled at the same time and it also requires professional guidance before operation. A user not familiar with the operation of the intestinal bypass liner may operate the intestinal bypass liner wrongly and discomfort the patients. Moreover, due to the problems of high manufacturing cost and technical limitations of the intestinal bypass liner, it is difficult to promote and apply the intestinal bypass liner in a wide range of the country. Therefore, providing a method for diabetes treatment without causing discomfort, or providing a device having a simple structure and a low cost and easy to be operated for diabetes treatment has become an important issue to be solved.

SUMMARY OF THE DISCLOSURE

In response to the above-referenced technical inadequacies, the present disclosure provides an intestinal barrier sleeve release system. The intestinal barrier sleeve release system guided by a gastroscope enters the duodenum and/or an upper part of the pylorus from the mouth through a guidewire, and separates the intestinal tissues from the food in the gastrointestinal tract, so as to improve insulin secretion and treat diabetes in a better way without hurting human body.

In one aspect, the present disclosure provides an intestinal barrier sleeve release system including a tubular housing having a first opening at one end and a second opening at the other end. A folded tubular sleeve to be released is disposed in the housing. The intestinal barrier sleeve release system further includes a release body and a push assembly. The release body is disposed at the first opening, connected to one end of the tubular sleeve, and made of a material that is able to be dissolved and absorbed in human intestines. The push assembly includes an inner sheath, a middle sheath and an outer sheath sequentially set and able to move relative to each other. The inner sheath is partially located in the housing and connected to the release body, the middle sheath has a piston stopper in the housing fixedly sleeved on an end, and the outer sheath is located outside the housing and has an end fixedly connected to the second opening. The inner sheath and the middle sheath are operated to move axially, the release body is disengaged from the housing, and the tubular sleeve moves out of the housing and is released at a specified position of the human intestines.

Preferably, the release body includes an internal core and a casing. The internal core has a body portion and a tubular sleeve connecting portion formed by extending the body portion. The tubular sleeve connecting portion is fixedly connected to the one end of the tubular sleeve. The casing covers the body portion and is connected to the first opening.

Preferably, an end of the inner sheath sequentially passes through the tubular sleeve connecting portion, the body portion and the casing of the internal core.

Preferably, a damper sheath is sleeved on a portion of the inner sheath passing out of the internal core.

Preferably, a surface of the body portion of the internal core and a surface of the casing facing a release direction of the tubular sleeve are round smooth surfaces.

Preferably, the body portion has an outer contour in a spherical or hemispherical shape, and the casing has an outer contour matches the outer contour of the body portion in shape, and covers the body portion outside.

Preferably, the body portion has an outer contour in a hemispherical shape, the tubular sleeve connecting portion is connected to a planar portion of the body portion, the casing is in a hemisphere shape and covers the body portion outside a hemispherical surface thereof, and an annular platform is formed on the periphery of an end surface of the hemispherical casing, and is abutted against the second opening of the housing.

Preferably, the internal core is physically connected to the casing.

Preferably, the other end of the tubular sleeve is fixedly connected to a stent, and the stent is an elastic memory alloy braided stent in a tubular mesh form.

Preferably, the middle sheath has a first extension end extending from the other end of the outer sheath, the first extension end is connected to a first handle, the first handle is provided with a Luer taper communicating the outside with the inside of the middle sheath, the inner sheath has a second extension end extending from the first extension end, and the second extension end is connected to a second handle.

In comparison with conventional technology, the intestinal barrier sleeve release system of the present disclosure has a simple structure, relatively few parts and low manufacturing cost. Implanting the intestinal barrier sleeve release system in a human body will not leave wounds in intestines, and is considered a low risk surgery operated by simple pushes, such that patients can suffer less pain and recover quickly after surgery. Unlike operating conventional equipment which is complicated in structure and has multiple lines to be pulled, people after simple training can operate the intestinal barrier sleeve release system of the present disclosure correctly and effectively. Moreover, the intestinal barrier sleeve release system of the present disclosure can be used to assist the extension of a soft catheter and the observation of gastrointestinal peristalsis. After implantation, the release body gradually disintegrates, is decomposed by digestive juices and is absorbed in the human body, and barium sulfate is excreted through the intestines, such that the intestinal barrier sleeve release system is safe to the human body. Therefore, after implanting the intestinal barrier sleeve of the present disclosure, the symptoms of type 2 diabetes and obesity can be greatly improved. Since patients do not need to have a diet anymore, they can have a better quality of your life.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
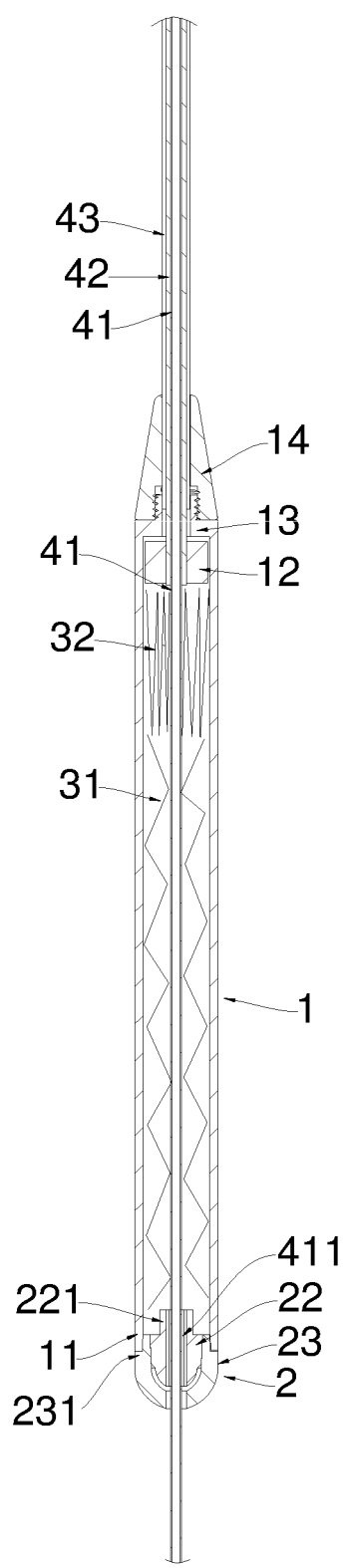
FIG. 1 is a cross sectional view of an intestinal barrier sleeve release system according to an embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
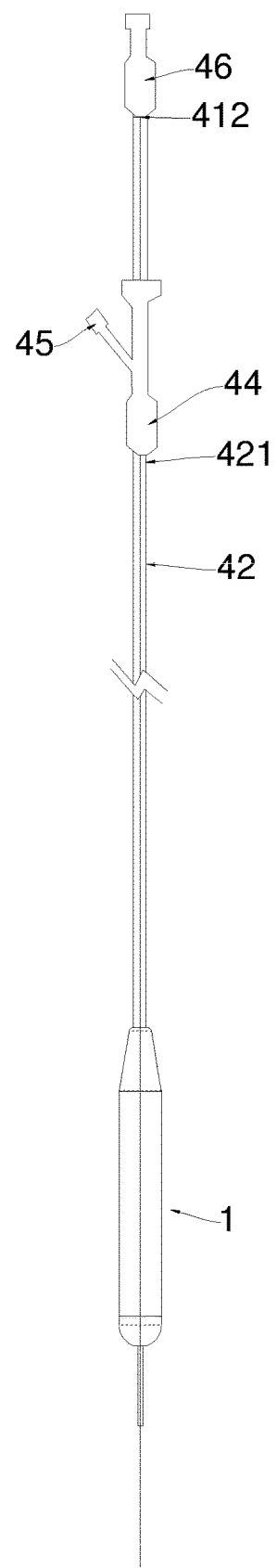
FIG. 2 is a schematic view of the entire structure of the intestinal barrier sleeve release system according to the embodiment of the present disclosure.

Referring to FIG. 1 and FIG. 2, an intestinal barrier sleeve release system is provided in an embodiment of the present disclosure. The intestinal barrier sleeve release system includes a housing 1, a release body 2 and a push assembly. The housing 1 is tubular and has a first opening 11 at one end and a second opening 13 at the other end. A folded tubular sleeve 31 to be released disposed in the housing 1. The release body 2 is disposed at the first opening 11, connected to one end of the tubular sleeve 31, and made of a material that is able to be dissolved and absorbed in human intestines. The push assembly includes an inner sheath 41, a middle sheath 42 and an outer sheath 43 sequentially set and able to move relative to each other. The inner sheath 41 is partially located in the housing 1 and connected to the release body 2. An end of the middle sheath 42 extends into the housing 1 through the second opening 13 and has a piston stopper in the housing 1 fixedly sleeved thereon. The outer sheath 43 is located outside the housing 1 and has an end fixedly connected to the second opening 13. The inner sheath 41 moves axially toward an operator to disengage the release body 2 from the housing 1. The inner sheath 41 and the middle sheath 42 drive the tubular sleeve 31 to move out of the housing 1 and to release at a specified position of the human intestines. The movement of the inner sheath 41 drives the release body 2 to move, and drives the tubular sleeve 31 to release. The middle sheath 42 move axially to drive the piston stopper 12 to push against the tubular sleeve 31 (i.e. pushing against an end of the tubular sleeve 31 which is not connected to the release body 2) so that the tubular sleeve 31 is pushed out of the housing 1.

Further, referring to FIG. 2, a protrusion is provided outside the second opening 13 of the housing 1 and has a nut 14 screwed thereon. The outer sheath 43 passes through the nut 14 and is fixedly connected to the second opening 13 of the housing 1. Specifically, the outer sheath 43 can be fixedly connected to the second opening 13 by sticking, thermal shrinkage, or other manners.

In this embodiment, the housing 1 and each part of the push assembly is made of one or more composite materials of polyurethane, polyethylene, and fluoropolymer. Aside from good support performance, pushability, toughness and a smooth surface to be smoothly pushed via an endoscope or in the tracts of the human body, also these materials is not easy to be bent and can be well controlled.

Specifically, in the use of the intestinal barrier sleeve release system of the present disclosure, a guidewire is passed through the inner sheath 41, the operator passes the entire system through the mouth, in cooperation with, the system is guided by the guidewire in cooperation with the gastroscope to the duodenum and/or an upper part of the pylorus. The guidewire and the push assembly guide and support the movement of the inner sheath 41 in the esophagus and gastrointestinal tract, so that the casing 1 and tubular sleeve 31 of the intestinal barrier sleeve release system can successfully reach the specified position. Then, the middle sheath 42 and the inner rube 41 in the push assembly are operated to release the tubular sleeve 31 in the casing 1 into the gastrointestinal tract, and the inner sheath 41 is operated to move the release body 2 to unfold the folded tubular sleeve 31. After the release body 2 made of a material that can be dissolved and absorbed in the human intestinal tract enters the intestines, it can be dissolved or decomposed in a short period of time by digestive juices or water, and then be dissolved and absorbed in the intestines, thereby completing the release of the tubular sleeve 31. In this way, a thin-film guide tube forms on the intestinal tissues to prevent and slow down nutrient absorption in the intestinal tract, and regulate the secretion of digestive enzymes, thereby regulating blood sugar and lipid levels and body weight, and avoiding the occurrence of diabetes. The release body 2 is made of a material which meets a biological safety requirement, can be dissolved or decomposed in the human body, and has no toxicity or side effects for the human body. The material may be, for example, one or more compounds of an edible gelling agent, a soy protein powder, starch, a polysaccharide compound, glycerin, branched or amylopectin, and the like. During formulation, the one or more compounds are added, mixed with water and a fat-soluble substance, and then solidified in a corresponding mold, to form a hard solid structure. Moreover, the release body 2 can also be made of a material which can be dissolved but not absorbed in the human body, and completely eliminated from the human body, without toxicity or side effect.

Figure 3:
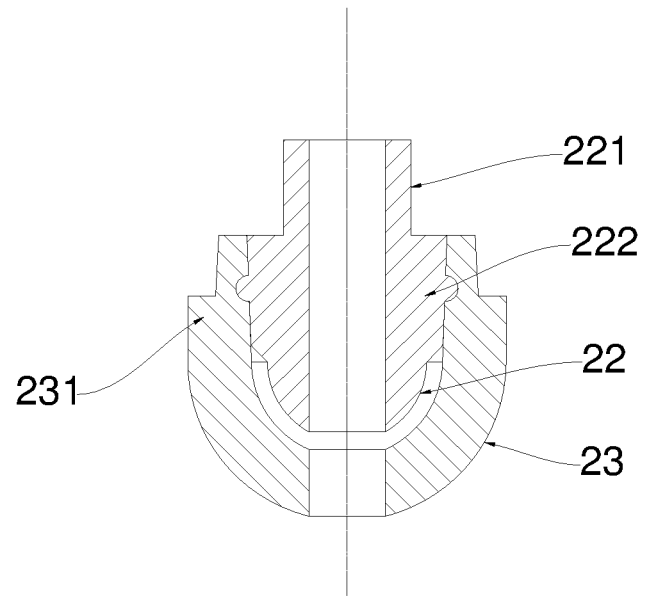
FIG. 3 is a cross sectional view of a structure of a release body of the intestinal barrier sleeve release system according to the embodiment of the present disclosure.
Figure 4:
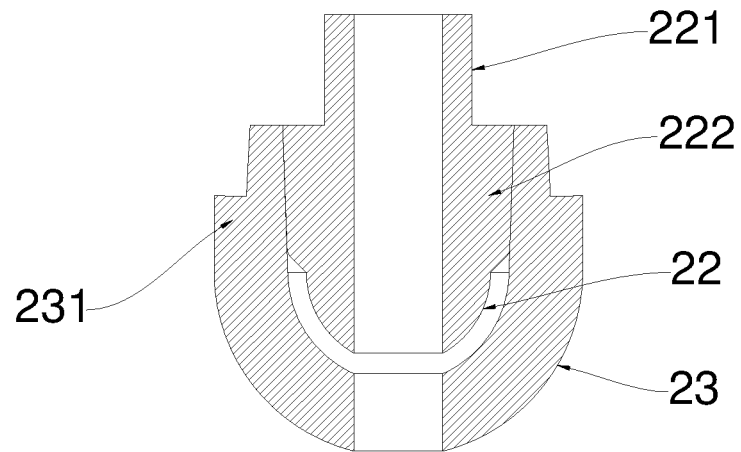
FIG. 4 is a cross sectional view of another structure of the release body of the intestinal barrier sleeve release system according to the embodiment of the present disclosure.

Preferably, referring to FIG. 3 to FIG. 4, the release body 2 includes an internal core 22 and a casing 23. The internal core 22 has a body portion 222 and a tubular sleeve connecting portion 221 connected to the one end of the tubular sleeve 31. The casing 23 covers the body portion 222 outside, is connected to the first opening 11 and is easily broken under force.

Preferably, referring to FIG. 3 and FIG. 4, a surface of the body portion 222 of the internal core 22 and a surface of the casing 23 facing a release direction of the tubular sleeve 31 are round smooth surfaces, which facilitates the movement of the release body 2 in the human intestinal tract.

Specifically, referring to FIG. 3 and FIG. 4, the body portion 222 has an outer contour in a spherical or hemispherical shape. The casing 23 has an outer contour matches the outer contour of the body portion 222 in shape, and covers the body portion outside. In this embodiment, the body portion 222 has the outer contour in a hemispherical shape, and the casing 23 has the outer contour in a hemispherical shape. In addition, the body portion 222 and the casing 23 can be approximately shaped like a sphere or hemisphere.

Preferably, referring to FIG. 3 and FIG. 4, the body portion 222 has the outer contour in a hemispherical shape, the tubular sleeve connecting portion 221 is connected to a planar portion of the body portion 222, the casing 23 is in a hemisphere shape and covers the body portion 222 outside a hemispherical surface thereof. An annular platform 231 is formed on the periphery of an end surface of the hemispherical casing 23, and is abutted against the second opening 13 of the housing 1.

Referring to FIG. 3 and FIG. 4, based on the above, the internal core 22 is physically connected to the casing 23 by, for example, screwing or engaging as shown. Specifically, FIG. 3 shows the screwed inner core 22 and casing 23. The internal core 22 and the casing 23 both include a portion in an approximately spherical shape and a portion in a cylindrical shape, and have threads engaged with each other on the portions in a cylindrical shape of the internal core 22 and the casing 23. FIG. 4 shows the engaged inner core 22 and casing 23. An outer surface of the internal core 22 and an inner wall of the casing 23 are respectively provided with fasteners which can be engaged to each other. It should be noted that the connection manner between the internal core 22 and the casing 23 is not limited to screwing or engaging, and can be a taper fit or other connection manners. For example, the casing 23 and the internal core 22 are taper-fitted to each other. Other similar structures are not described in detail herein.

Preferably, referring to FIG. 2, an end of the inner sheath 41 sequentially passes through the tubular sleeve connecting portion 221 and the body portion 222 of the internal core 22, and the casing 23, and extends out of the first opening 11 to allow an endoscope to inspect the intestinal tract. In this embodiment, the inner sheath 41 forms a tight fit or an interference fit with the tubular sleeve connecting portion 221 and the body portion 222 of the internal core 22, and the housing 23, such that the inner sheath 41 can drive the release body 2 to move toward the release direction of the tubular sleeve 31 and the tubular sleeve 31 to be unfolded and to extend out of the housing 1. The tubular sleeve connecting portion 221, the body portion 222 and the casing 23 can be connected to the inner sheath 41 in different manners.

Preferably, referring to FIG. 1, a damper sheath 411 is sleeved on a portion of the inner sheath 41 passing out of the internal core 22. In this embodiment, a tight fit is formed between the inner sheath 41 and the internal core 22 via the damper sheath 411. The damper sheath 411 is used to increase sliding friction between the release body 2 and the inner sheath 41, thereby enhancing the capability of the inner sheath 41 to drive the release body 2 to move.

In this embodiment, the damper sheath 411 can be made from one or more elastic materials of polyurethane, silicone, and TPE, with a surface subjected to physical or chemical processing to increase friction. Accordingly, before the tubular sleeve 31 is released, the damper sheath 411 maintains a relatively static state between the release body 2 and the inner sheath 41.

Preferably, referring to FIG. 2, the other end of the tubular sleeve 31 is fixedly connected to a stent 32, and the stent is an elastic memory alloy braided stent in a tubular mesh form. Specifically, the stent 32 can be made of a nickel-titanium alloy, stainless steel, other elastic metal or other qualified memory alloys, meeting a biocompatibility requirement and suitable for long-term implantation in the human body. The stent 32 is regularly arranged in the shape of a rhombus, hexagon, or honeycomb, and placed in the duodenal bulb. The stent is elastic and can vary in shape with the peristalsis of the intestinal tract. Also, it has a certain supporting force and can be fixed in the duodenal bulb.

Specifically, during the operation of the middle sheath 42, the middle sheath 42 drives the piston stopper 12 to push the stent 32 and the tubular sleeve 31 outward from the housing 1 while the operator has to observe the stent 32 in the housing 1 via the endoscope. When the front end of the stent 32 is about to be out of the housing 1, the operation of the middle sheath 42 should be stopped immediately. At the same time, the operator has to adjust the position of the housing 1 of the intestinal barrier sleeve release system so that the stent 32 can be fixed in the duodenal bulb when leaving the housing 1.

Specifically, based on the above, the structure used to operate the movement of the middle sheath 42 and the inner sheath 41 includes a first extension end 421 and a first handle 44, a Luer taper 45, a second extension end 412 and a second handle 46. The middle sheath 42 has the first extension end 421 extending out of the outer sheath 43, the first extension end 421 is connected to the first handle 44, the first handle 44 is provided with a Luer taper 45 communicating the outside with the inside of the middle sheath 42, the inner sheath 41 has the second extension end 412 extending from the first extension end 421, and the second extension end 412 is connected to the second handle 46.

Specifically, in the process of operating the middle sheath 42 and the inner sheath 41 to release the tubular sleeve 31, the operator can add a certain amount of water or saline through the Luer taper 45. As the water or saline enters the tubular sleeve 31 through a gap between the middle sheath 42 and the inner sheath 41, the release of the tubular sleeve 31 in the duodenum and the dissolution or decomposition of the release body 2 can be accelerated. When the tubular sleeve 31 is released, the tubular sleeve 31 and the release body 2 move from the duodenum towards the jejunum with the peristalsis of the intestinal tract for about 1 to 10 minutes. At the same time, as the saline flows towards the tubular sleeve 31 along the gap between the inner sheath 41 and the middle sheath 42, the movement of the tubular sleeve 31 and the release body 2 towards the jejunum and the release of the tubular sleeve 31 are also accelerated. The tubular sleeve 31 may contain a developing material, such as barium sulfate, bismuth carbonate, and tungsten, which can be developed under X rays. The release body 2 may also contain a developing material so as to provide its position under X rays, thereby facilitating the operation.

The intestinal barrier sleeve release system of the present disclosure can be operated as follows. Firstly, the inner sheath 41 is pulled by and towards the operator, such that when the first opening 11 of the housing 1 is pressed against the casing 23, the annular platform 231 of the casing 23 is disconnected to separate the release body 2 from the housing 1. Then, the inner sheath 41 is operated to move the release body 2 away from the operator (i.e. into the body of a patient), such that one end of the tubular sleeve 31 extends out of the housing 1 and drives the tubular sleeve 31 to be unfolded. In this case, the middle sheath 42 is then operated to drive the piston stopper 12 to move. The piston stopper 12 pushes the stent 32 on the other end of the tubular sleeve 31 in the housing 1 to push the whole tubular sleeve 31 out of the housing 1. It should be noted that when the tubular sleeve 31 is completely unfolded and the piston stopper 12 pushes the stent 32 to move to the first opening 11 of the housing 1 (when the tubular sleeve 31 is about to be completely released), the stent 32 has to arrive at a specified release position in the intestinal tract (an appropriate position near the duodenum of the stomach pylorus and/or the upper portion of the stomach pylorus in the stomach of the body). Then, the second handle 46 is pushed in a direction away from the operator so that the stent 32 is completely detached from the housing 1 and fixed in the duodenal bulb. The stent is elastic and can vary in shape with the peristalsis of the intestinal tract. Also, it has a certain supporting force and can be fixed in the duodenal bulb. The unfolded tubular sleeve 31 may be placed in the digestive tract for 1 to 12 months, and the duration can be adjusted according to disease conditions or actual conditions.

In this embodiment, there is still another way of operation described as follows. When the middle sheath 42 and the inner sheath 41 are simultaneously operated to move the piston stopper 12 to push one end of the tubular sleeve 31 in the housing 1, the inner sheath 41 moves to drive the release body 2 to move, and the release body 2 drives the stent 32 on the other end of the tubular sleeve 31. In this way, the tubular sleeve 31 is unfolded and extends out of the housing 1. Finally, the whole tubular sleeve 31 is pushed out of the housing 1 at a specified release position in the intestinal tract.

Accordingly, the tubular sleeve 31 may be made from one or more composite materials of polyurethane, polyethylene, fluoropolymer, and silicone, which are soft and elastic and have a smooth surface such that food residues are less likely to be left at the inner wall of the tubular sleeve 31. The material thereof meets a biocompatibility requirement, and does not cause an allergy or other adverse effects to the human body during long-term implantation.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An intestinal barrier sleeve release system, including a tubular housing having a first opening at one end and a second opening at the other end, a folded tubular sleeve to be released disposed in the housing, the intestinal barrier sleeve release system comprising:

a release body disposed at the first opening, fixedly connected to one end of the tubular sleeve, and made of a material that is able to be dissolved and absorbed in human intestines, the release body including:

an internal core having a body portion and a tubular sleeve connecting portion formed by extending the body portion, the tubular sleeve connecting portion fixedly connected to the one end of the tubular sleeve; wherein the body portion has an outer contour in a hemispherical shape, and the tubular sleeve connecting portion is connected to a planar portion of the body portion; and a casing being in a hemisphere shape and covering the body portion; wherein an annular platform is formed on the periphery of an end surface of the hemispherical casing, and is abutted against the first opening of the housing; wherein the annular platform is configured to be broken under force;

a push assembly including an inner sheath, a middle sheath and an outer sheath sequentially set and able to move relative to each other, the inner sheath partially located in the housing and connected to the release body, the middle sheath having a piston stopper in the housing fixedly sleeved on an end of the middle sheath that is adjacent to the tubular sleeve, and the outer sheath located outside the housing and having an end fixedly connected to the second opening;

wherein, after the annular platform is broken under the force, the inner sheath and the middle sheath are operated to move axially in a direction toward the first opening, the release body is disengaged from the housing, so as to move the tubular sleeve out of the housing and to be released at a specified position of the human intestines.

2. The intestinal barrier sleeve release system according to claim 1, wherein an end of the inner sheath sequentially passes through the tubular sleeve connecting portion, the body portion and the casing of the internal core.

3. The intestinal barrier sleeve release system according to claim 2, wherein the internal core is physically connected to the casing.

4. The intestinal barrier sleeve release system according to claim 2, wherein a damper sheath is sleeved on a portion of the inner sheath passing out of the internal core.

5. The intestinal barrier sleeve release system according to claim 4, wherein the internal core is physically connected to the casing.

6. The intestinal barrier sleeve release system according to claim 1, wherein a surface of the body portion of the internal core and a surface of the casing facing a release direction of the tubular sleeve are round smooth surfaces.

7. The intestinal barrier sleeve release system according to claim 6, wherein the internal core is physically connected to the casing.

8. The intestinal barrier sleeve release system according to claim 1, wherein the casing has an outer contour matches the outer contour of the body portion in shape.

9. The intestinal barrier sleeve release system according to claim 8, wherein the internal core is physically connected to the casing.

10. The intestinal barrier sleeve release system according to claim 1, wherein the internal core is physically connected to the casing.

11. The intestinal barrier sleeve release system according to claim 1, wherein the other end of the tubular sleeve is fixedly connected to a stent, and the stent is an elastic memory alloy braided stent in a tubular mesh form.

12. The intestinal barrier sleeve release system according to claim 1, wherein the middle sheath has a first extension end extending from the other end of the outer sheath, the first extension end is connected to a first handle, the first handle is provided with a Luer taper communicating the outside with the inside of the middle sheath, the inner sheath has a second extension end extending from the first extension end, and the second extension end is connected to a second handle.

* * * * *